(12) United States Patent
Wang

(10) Patent No.: US 6,293,918 B1
(45) Date of Patent: Sep. 25, 2001

(54) ADJUSTABLE SPLINT

(76) Inventor: Tzu C. Wang, 11848 Taylorcrest, Houston, TX (US) 77024

( * ) Notice: Subject to any disclaimer, the term of this patent is extended or adjusted under 35 U.S.C. 154(b) by 0 days.

(21) Appl. No.: 09/407,480

(22) Filed: Sep. 28, 1999

(51) Int. Cl.$^7$ .................................. A61F 5/00; A61F 5/37
(52) U.S. Cl. ............................ 602/20; 602/16; 602/21; 128/878; 128/881; 128/879
(58) Field of Search .................... 602/5, 16, 20–21, 602/23, 26–27, 60–65; 2/22, 455, 16; 128/878, 881, 882; 473/59, 62, 63

(56) References Cited

U.S. PATENT DOCUMENTS

| | | | |
|---|---|---|---|
| 4,054,130 | * 10/1977 | Franke | 128/87 R |
| 4,618,147 | * 10/1986 | Hurd et al. | 473/62 |
| 4,666,158 | * 5/1987 | Moro | 473/62 |
| 4,790,300 | * 12/1988 | Marx | 128/84 |
| 5,163,678 | * 11/1992 | Rogers | 2/16 X |
| 5,570,881 | * 11/1996 | Lau | 602/16 |
| 5,732,411 | * 3/1998 | Coleman et al. | 2/22 |
| 5,851,194 | * 12/1998 | Fratrick | 602/28 |
| 6,076,185 | * 6/2000 | Schramm | 602/62 X |

* cited by examiner

*Primary Examiner*—Denise Pothier
(74) *Attorney, Agent, or Firm*—Trop, Pruner & Hu, P.C.

(57) ABSTRACT

An adjustable splint which provides for self-locking adjustment in one of a plurality of selectable positions. The splint comprises a first rigid member for supporting a first portion of a limb of a patient and a second rigid member for supporting a second portion of that limb, on opposite sides of a joint. A pivot connects the first and second members. A releasable clasp lies along the limb of the patient, arranged so that fastening the splint to the limb effectively locks the clasp in the selected position. In one embodiment, the clasp comprises a leaf spring attached to the first member. At a free end of the spring, a latch is provided which engages one of a plurality of notches in the second member.

19 Claims, 4 Drawing Sheets

ADJUSTABLE SPLINT

FIELD OF THE INVENTION

This invention relates generally to therapeutic braces and, more particularly, to an adjustable splint for therapeutic support of a limb of a patient at a joint.

BACKGROUND ART

Splints or braces are typically used to hold joints of a limb, such as wrist or elbow joints, in a neutral position to promote healing of bone or other tissue. The angle at which these splints hold the joint has generally not been adjustable. The degree of flexation or extension of the joint, however, may vary from patient to patient and may even vary in an individual patient depending on the progress of the patient's therapy. For example, after a stroke or after the onset of a muscle attacking disease, for example, nerve palsy, a patient's hand may become closed or clenched and the wrist may be involuntarily fixed in a palmarflexion position. To restore the use of the hand, the patient may undergo a therapy to open the clenched fist and to urge the wrist towards a more neutral position. This can be accommodated by a splint, which can be adjustable at the joint to assume different positions. Such an adjustable splint for a wrist brace has been proposed by Klotz in U.S. Pat. 5,358,471. The mechanism proposed by Klotz, however, involves installing either individual machine screws or bolts and wing nuts at medial and lateral sides of the splint. There remains a need for improvement of such a splint to provide an easier mechanism for selecting the angle of flexion of the splint.

SUMMARY OF THE INVENTION

I have invented an adjustable splint, which provides for self-locking adjustment in one of a plurality of selectable positions. The splint comprises a first rigid member for supporting a first portion of a limb of a patient and a second rigid member for supporting a second portion of that limb, on opposite sides of a joint. A pivot is provided connecting the first and second members with a swivel having an axis that can be aligned with an axis of bending in the joint of the limb. A releasable clasp is provided which lies along the limb of the patient. The clasp is arranged so that fastening the splint to the limb effectively locks the clasp in the selected position. In my preferred embodiment, the clasp comprises a leaf spring attached to the first member. At a free end of the spring, a latch is provided which engages one of a plurality of notches in the second member. A cavity is provided in the second member, adapted to receive the free end of the spring so that the inside of the second member and the inside of the leaf spring generally form a surface that conforms to the limb of a patient. In one embodiment, the splint is bilaterally symmetrical and can be used on either right or left limbs, for example, at right or left wrists of a patient.

It is an object, therefore, of my invention to provide an adjustable splint for supporting a limb of a patient.

It is also an object of my invention to provide such an adjustable splint with a mechanism for selecting one of a plurality of positions.

Another object of my invention is to provide a splint that is locked into a selected position by the action of mounting the splint on the limb of the patient.

A further object of my invention is to provide a splint, which can be used on limbs on either side of the body.

These and other objects and features of my invention will be apparent from the following detailed description, taken with reference to the accompanying drawings.

DETAILED DESCRIPTION

Figure 1:
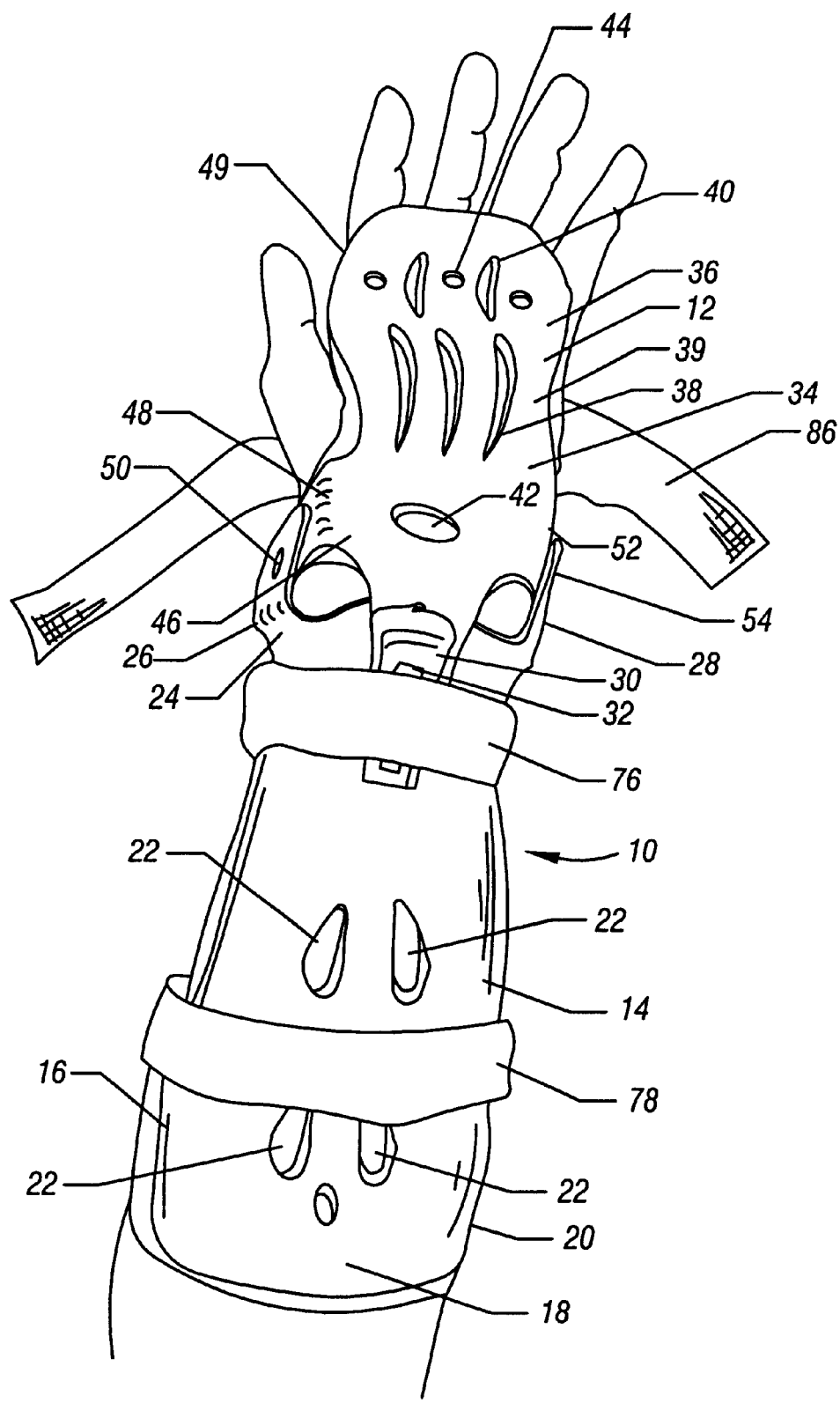
FIG. 1 is a prospective view of a splint according to my invention, in particular a wrist splint, illustrated supporting a forearm and hand of a patient.

Reference will now be made to the accompanying drawings in which like numerals are used to designate like parts throughout. FIG. 1 illustrates an inferior perspective view of a splint 10 according to my invention. In this embodiment, the splint comprises a wrist splint. My invention, of course, can be used for other joints of the body as well. The splint comprises a first substantially rigid member 12 or hand support and a second substantially rigid member 14 or forearm support. The first and second members 12, 14, are adapted to conform generally to their adjacent limb portion. The hand support 12 is, for example, adapted to conform generally to the palm of the hand. The forearm support 14 is adapted to conform generally to the shape of the forearm. The forearm support 14 comprises a lateral side 16, a bottom 18, and a medial side 20. Along the forearm support 14, ventilation holes 22 may be provided at selected locations. Such holes reduce the weight of the splint and provide for ventilation. The number and placement of such holes 22 is largely a matter of design discretion. At a distal end 24 of the forearm support 14, a lateral pivot arm 26 extends distally from a lateral side 16 of the support. A medial pivot arm 28 similarly extends distally from the medial side 20 of the support. Also at the distal end 24, an exterior cavity 30 extends generally longitudinally at the distal end of the support 14. The function of this cavity will be explained in more detail hereafter.

Figure 2:
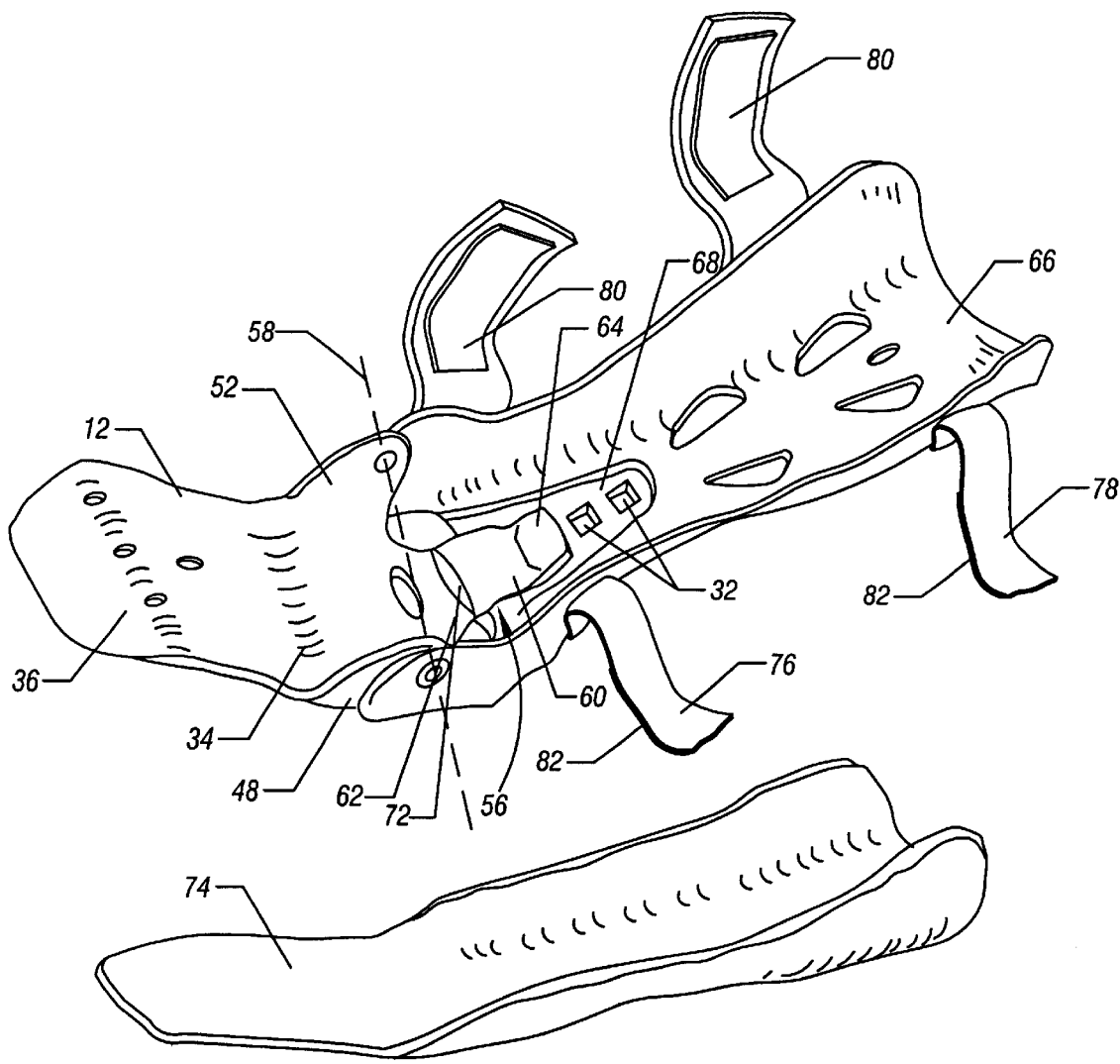
FIG. 2 is an exploded prospective drawing of the splint of FIG. 1.

The hand support 12 comprises a palm segment 34 and a finger segment 36. The palm segment 34 lies generally proximately and adjacent the distal end of the forearm segment 14. It preferably has a slightly concave shape longitudinally on the side adjacent the patient's hand. The finger segment 36 extends distally and has a generally convex shape on the side adjacent the patient's hand. This can best be seen in FIG. 2. On an exposed side 39 of the hand segment 12, as seen in FIG. 1, the palm segment 34 is slightly convex and the finger segment 36 is concave. Additional rigidity for the hand segment 12 is provided by convex struts 38 on the palm segment and by concave struts 40 on the finger segment. Ventilation holes 44 may be provided in the finger segment, according to design discretion.

Figure 3:
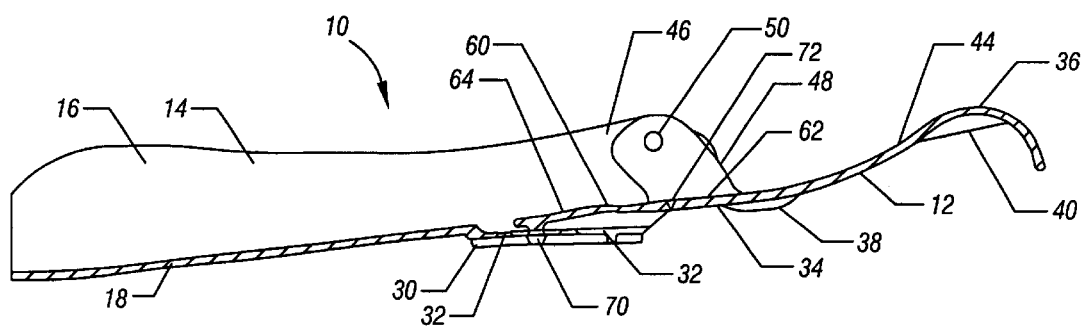
FIG. 3 is a plan view section of rigid members of the splint of FIGS. 1 and 2.

At a proximal end 46 of the hand support 12, a lateral pivot arm 48 engages the lateral pivot arm 26 of the forearm support. The two lateral pivot arms 26, 48 are connected by a swivel 50, which may be a rivot or other fastener. On other medial side, a medial pivot arm 52 on the hand support 12 engages the medial pivot arm 28 of other forearm support 14. A swivel 54 also connects the medial pivot arms. The swivels 50, 54 preferably have parallel axes and most preferably share a common axis configured to lie parallel to an axis of bending of other adjacent joint, in this instance, the wrist. The two swivels 50, 54 form a pivot that permits the joint, that is, the wrist, to be placed in a selected degree of flexion. The degree of flexion is selected using a self-locking clasp, which will now be described in connection with FIGS. 2, 3, and 4.

Figure 4:
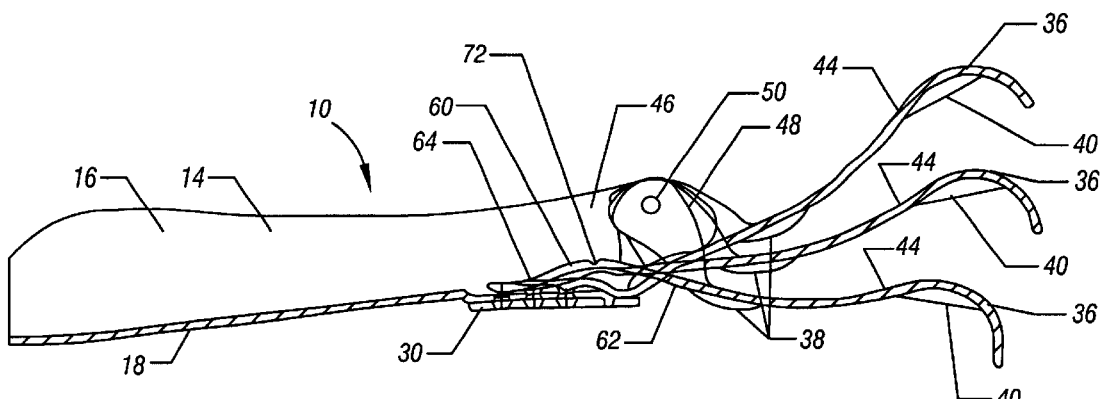
FIG. 4 is a plan view section similar to FIG. 3, illustrating multiple positions for a hand-supporting member of the splint.

The clasp 56 of my invention lies between the two swivels 50, 54 along a plane which generally bisects the splint 10 and is generally perpendicular to the axis 58 of the pivot for swivels 50, 54. The clasp 56 preferably comprises a leaf spring 60 having a first end 62 attached to the first member, for example the hand support 12 and a second free end 64 which presses against the bottom 18 of the second member or forearm support 14 on an interior side 66. The leaf spring 60 preferably rides in an interior cavity 68 and engages the notches 32 with a latch 70 seen in FIG. 3. The latch 70 engages a selected one of the notches 32 to adjust the position of the first member or hand support 12 with respect to the second member or forearm support 14 as illustrated in FIG. 4. The number of notches is a matter of design discretion. I have illustrated three notches in my preferred embodiment. To control the spring action of the leaf spring 60, a relieved portion 72 may be provided at the first end of the leaf spring. In addition, an elliptical hole 42 in the palm segment serves both to provide ventilation and to increase the flexibility of the leaf spring 60. The elliptical shape of the hole, with a major axis perpendicular to the length of the leaf spring, effectively de-couples the first end 64 of the spring 60, allowing the spring to bend more freely. A foam pad 74 is generally provided to fit within the rigid members of the splint to provide additional comfort.

The action of the clasp permits splints to be quickly oriented into a desired configuration or selected angle. When the limb of the patient is placed in the splint, the limb presses against the leaf spring 60 holding the latch 70 in a selected notch. Because the leaf spring 60 is substantially within the cavity of 68 the pressure of the splint against the forearm is generally uniform and the leaf spring does not abrade or irritate the arm of the patient. Straps 76, 78 may be provided to secure the splint 10 to the limb of the patient. Loop and eye fasteners 80, 82 may be provided to join the ends of the straps 76, 78. The straps may be attached to the splint, or may be separate portions. A distal strap 76 preferably passes generally over the location of the clasp 56. This provides a secure pressure to hold the leaf spring 60 in engagement with the notches 32. The exterior cavity 30, described above, generally acts to prevent the strap 76 from coming in direct contact with the latch 70 so that the latch 70 will not be pressed out of a notch 32. Raised edges 84 around the exterior cavity 30 provide additional space between the strap 76 and the latch 70 to prevent contact with the latch 70 when, for example, a patient might rest their forearm on a table or other surface.

The patient's hand may similarly be secured to the hand support 12 using a strap or other fasteners such as a gauze bandage 86. In one embodiment, the splint 10 is bilaterally symmetrical, such that it can be used on right or left limbs, in particular at right or left wrists. The splint of my invention may be formed of injection-molded plastic or other suitable material. Where plastic is used, features such as the elliptical hole 42 and the relieved portion 70 become particularly important for controlling the flexibility of the leaf spring 60.

Figure 5:
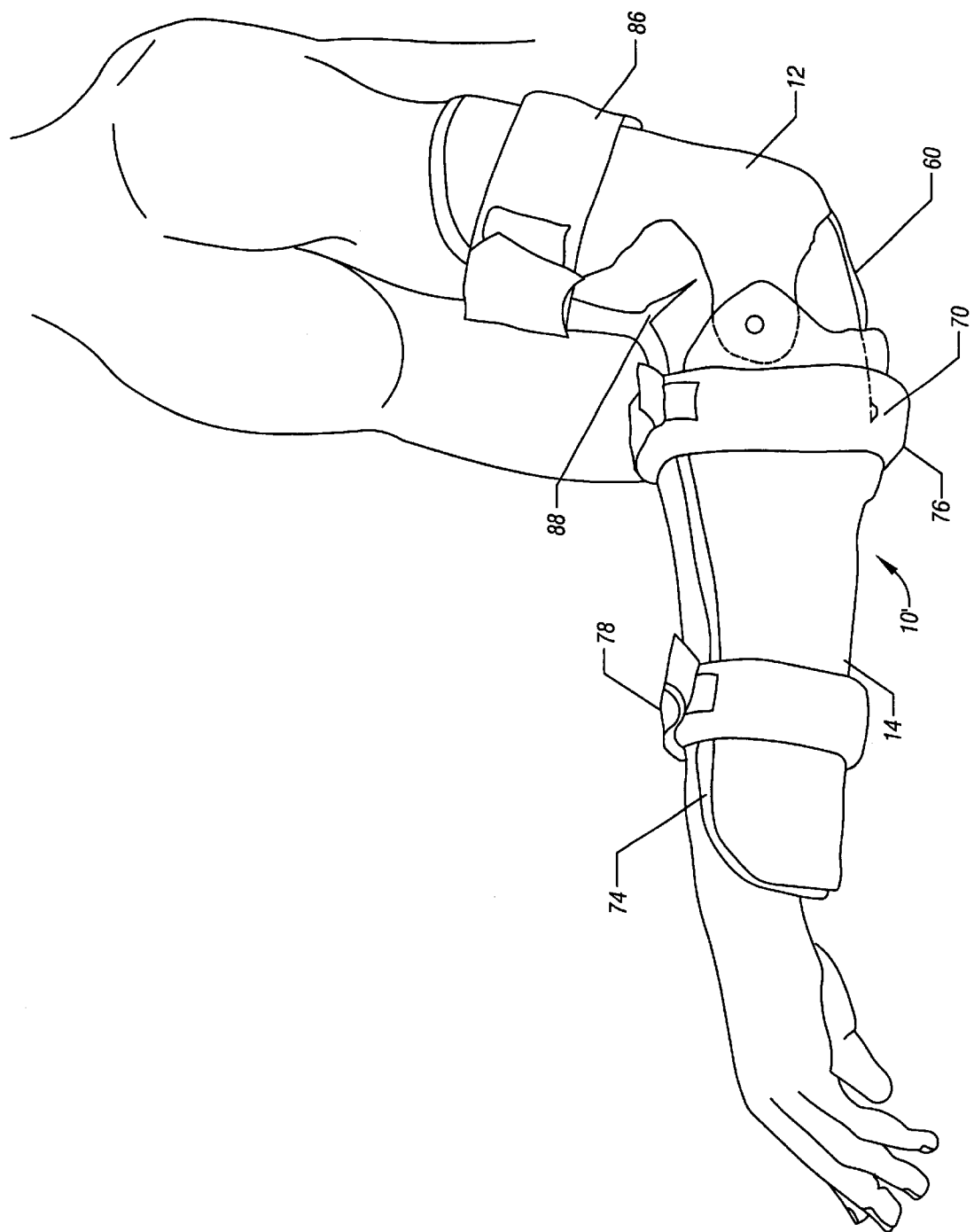
FIG. 5 is a plan view of an elbow splint, according to my invention, shown supporting the upper arm and forearm of a patient.

My invention may also be used for splints for other joints of the body as, for example the elbow as illustrated in FIG. 5. In the embodiment of FIG. 5 the splint 10 has the first rigid member 12 formed as a support for the upper arm and the second rigid member 14 formed as a support for the forearm. The spring 60 can be seen in phantom lines under the second rigid member 14, such that the latch 70 is under the strap 76. The pad 74 may have darts 88 cut or provided near the elbow joint to accommodate a relatively large degree of bending provided in this embodiment.

The foregoing examples of embodiments of my invention should be deemed exemplary only. Those skilled in the art will recognize that changes and modifications could be made in the design or construction without departing from the scope or teachings of my invention. It is intended, therefore, that the scope of my invention should be defined by the accompanying claims.

What is claimed is:

1. An adjustable splint for an injured limb of a patient, the splint comprising:

a first substantially rigid member shaped to conform to a first portion of said limb;

a second substantially rigid member shaped to conform to a second portion of said limb, said second member being adjacent said first member and having a plurality of notches therein;

a pivot connecting said first and second members, said pivot having an axis which can be aligned with an axis of bending of a joint of said limb between said first and second portions of said limb; and a spring attached to said first member at a first end of said spring, and having a latch at a second end of said spring, said latch selectively engaging one of said notches, wherein said spring comprises a leaf spring.

2. The splint of claim 1 further comprising a strap for binding said splint to the limb, said strap being attached to said second member near said notches such that said strap holds the limb against said spring to hold said latch in said selected notch.

3. The splint of claim 1 wherein said spring is next to the pivot.

4. An adjustable splint for an injured limb of a patient, the splint comprising:

a first substantially rigid member shaped to conform to a first portion of said limb;

a second substantially rigid member shaped to conform to a second portion of said limb, said second member being adjacent said first member and having a plurality of notches therein;

a pivot connecting said first and second members, said pivot having an axis which can be aligned with an axis of bending of a joint of said limb between said first and second portions of said limb; and a spring attached to said first member at a first end of said spring, and having a latch at a second end of said spring, said latch selectively engaging one of said notches, wherein said second member further comprises a first cavity, said notches being in said first cavity and said second end of said spring lying in said first cavity to engage said notches with said latch, and wherein said second member further comprises an exterior cavity opposite said first cavity.

5. The splint of claim 4 further comprising a strap for binding said splint to the limb, said strap being attached to said second member near said notches and passing over said exterior cavity such that said strap holds the limb against said spring to hold said latch in said selected notch without contacting said latch.

6. An adjustable splint for an injured limb of a patient, the splint comprising:

a first substantially rigid member shaped to conform to a first portion of said limb;

a second substantially rigid member shaped to conform to a second portion of said limb, said second member being adjacent said first member and having a plurality of notches therein;

a pivot connecting said first and second members, said pivot having an axis which can be aligned with an axis of bending of a joint of said limb between said first and second portions of said limb; and a spring attached to said first member at a first end of said spring, and having a latch at a second end of said spring, said latch selectively engaging one of said notches, wherein said first member and said second member are symmetrical laterally to enable the first member and second member to be used with either a left limb or a right limb of the patient.

7. A splint for an injured limb of a patient, the splint comprising:

a first substantially rigid member shaped to conform to a palm of a hand of the patient;

a second substantially rigid member shaped to conform to a forearm of the patient;

a pivot connecting said first and second members, said pivot having an axis which can be aligned with an axis of bending of a joint of said limb between the hand and the forearm; and a releasable clasp connecting said first and second members, said clasp being arranged along an axis of one of the first and second members that is generally perpendicular to said axis of said pivot, the releasable clasp to set the relative position of the first and second members for holding the hand and forearm in a target position, wherein the clasp comprises a leaf spring attached to one of the first and second members, and the other one of the first and second members comprising elements for engagement by the leaf spring.

8. The splint of claim 7, wherein the splint has a lateral side and a medial side, wherein said pivot comprises a first swivel mounted at the lateral side and a second swivel mounted at the medial side and said clasp is mounted between said first and second swivels.

9. The splint according to claim 7 wherein said first member and said second member are bilaterally symmetrical laterally to enable the first member and second member to be used with either a left limb or a right limb of the patient.

10. The splint of claim 7, wherein the first member has a palm segment to support the palm and a finger segment to support fingers of the patient.

11. The splint of claim 10, wherein the palm segment has a generally concave shape to receive the palm.

12. The splint of claim 10, wherein the finger segment has a generally convex shape to receive the fingers.

13. The splint of claim 7, wherein the elements comprise notches.

14. The splint of claim 7, wherein engagement of the leaf spring and the elements provide plural relative positions of the first and second members.

15. The splint of claim 7, wherein the first member has a contour conforming to the palm.

16. The splint of claim 7, wherein the pivot comprises a first pivot portion and a second pivot portion, the clasp positioned between the first and second pivot portions.

17. The splint of claim 7, wherein the pivot comprises a first pivot portion and a second pivot portion, the first and second pivot portions spaced apart to allow the hand or forearm of the user to be placed between the first and second portions.

18. A splint for use with a limb of a user, comprising:

a first member shaped to receive a first limb portion;

a second member having a side shaped to receive a second limb portion, the second member pivotally attached to the first member;

a clasp attached to the first member; and a plurality of elements provided on the side of the second member to receive the second limb portion, the clasp engageable in one of the plurality of elements to provide plural relative positions of the first and second members, wherein the clasp comprises a leaf spring to engage the plurality of elements.

19. The splint of claim 18, wherein the plurality of elements comprise a plurality of notches.

* * * * *

UNITED STATES PATENT AND TRADEMARK OFFICE
CERTIFICATE OF CORRECTION

PATENT NO. : 6,293,918 B1
DATED : September 25, 2001
INVENTOR(S) : Tzu C. Wang

It is certified that error appears in the above-identified patent and that said Letters Patent is hereby corrected as shown below:

Column 6,
Line 4, delete "bilaterally".

Signed and Sealed this

Fourteenth Day of May, 2002

*Attest:*

JAMES E. ROGAN
*Attesting Officer*     *Director of the United States Patent and Trademark Office*